US012568940B2

(12) United States Patent
Leighton et al.

(10) Patent No.: US 12,568,940 B2
(45) Date of Patent: Mar. 10, 2026

(54) TRANSGENIC CHICKEN HAVING AN ENDOGENOUS IMMUNOGLOBULIN HEAVY CHAIN GENE IN WHICH THE IgY CH1 CODING SEQUENCE IS FUNCTIONALLY DELETED

(71) Applicant: Crystal Bioscience Inc., San Diego, CA (US)

(72) Inventors: Philip A. Leighton, San Francisco, CA (US); William Don Harriman, Alameda, CA (US)

(73) Assignee: CRYSTAL BIOSCIENCE INC., Emeryville, CA (US)

( * ) Notice: Subject to any disclaimer, the term of this patent is extended or adjusted under 35 U.S.C. 154(b) by 958 days.

(21) Appl. No.: 15/734,535

(22) PCT Filed: Jun. 5, 2019

(86) PCT No.: PCT/US2019/035535
§ 371 (c)(1),
(2) Date: Dec. 2, 2020

(87) PCT Pub. No.: WO2019/241001
PCT Pub. Date: Dec. 19, 2019

(65) Prior Publication Data
US 2021/0227811 A1     Jul. 29, 2021

Related U.S. Application Data

(60) Provisional application No. 62/684,630, filed on Jun. 13, 2018.

(51) Int. Cl.
*A01K 67/027*     (2024.01)
*A01K 67/0278*     (2024.01)
*C12N 15/85*     (2006.01)

(52) U.S. Cl.
CPC ...... *A01K 67/0278* (2013.01); *C12N 15/8509* (2013.01); *A01K 2217/072* (2013.01); *A01K 2217/075* (2013.01); *A01K 2217/15* (2013.01); *A01K 2227/30* (2013.01)

(58) Field of Classification Search
None
See application file for complete search history.

(56) References Cited

U.S. PATENT DOCUMENTS 8,592,644 B2     11/2013     Harriman et al.
2017/0156298 A1*     6/2017     Harriman .............. C12N 15/87

FOREIGN PATENT DOCUMENTS

WO     WO 2011/019844 A1     2/2011

OTHER PUBLICATIONS

Schusser (Eur. J. Immunol., 2016, vol. 46, No. 9, p. 2137-2148) (Year: 2016).*
Leighton et al., "A diverse repertoire of human immunoglobulin variable genes in a chicken B cell line is generated by both gene conversion and somatic hypermutation", Frontiers in Immunology, 2015, 6(126):1-8.
Schusser et al., "Expression of heavy chain-only antibodies can support B-cell development in light chain knockout chickens", Eur. J. Immunol., 2016, 46: 2137-2148.
Anthony et al., "Biochemical Characterization of Patients With In-Frame or Out-of-Frame DMD Deletions Pertinent to Exon 44 or 45 Skipping", JAMA Neurol., 2014, 71(1): 32-40.
Barthelemy et al., "Comprehensive Analysis of the Factors Contributing to the Stability and Solubility of Autonomous Human VH Domains", The Journal of Biological Chemistry, 2008, 283(6): 3639-3654.
Chen et al., "Fusion Protein Linkers: Property, Design and Functionality", Adv Drug Deliv Rev., 2013, 65(10): 1357-1369.
Collarini et al., "Inserting random and site-specific changes into the genome of chickens", Poultry Science, 2015, 94: 799-803.
Da Silva et al, "IgY: A promising antibody for use in immunodiagnostic and in immunotherapy", Veterinary Immunology and Immunopathology, 2010, 135: 173-180.
Desmyter et al., "Antigen Specificity and High Affinity Binding Provided by One Single Loop of a Camel Single-domain Antibody", The Journal of Biological Chemistry, 2001, 276(28): 26285-26290.
Janeway et al., "The generation of diversity in immunoglobulins", Immunobiology: The Immune System in Health and Disease. 5th edition, 2001, 12 pages.
Nilvebrant et al. "Engineered autonomous human variable domains", Curr Pharm Des., 2016, 22(43): 6527-6537.
Schusser et al., "Harnessing Gene Conversion in Chicken B Cells to Create a Human Antibody Sequence Repertoire", PLOS One, 2013, 8(11): e80108, pp. 1-15.
Schusser et al., "Immunoglobulin knockout chickens via efficient homologous recombination in primordial germ cells", PNAS, 2013, 110(50): 20170-20175.
Watson et al., "Complete Haplotype Sequence of the Human Immunoglobulin Heavy-Chain Variable, Diversity, and Joining Genes and Characterization of Allelic and Copy-Number Variation", The American Journal of Human Genetics, 2013, 92: 530-546.

(Continued)

*Primary Examiner* — Michael C Wilson
(74) *Attorney, Agent, or Firm* — James S. Keddie; Bozicevic, Field & Francis LLP

(57)     ABSTRACT

Provided herein is a transgenic chicken comprising a genome having an endogenous immunoglobulin heavy chain gene in which the IgY CH1 coding sequence is functionally deleted. In certain embodiments, in B cells of the chicken the endogenous immunoglobulin heavy chain gene comprises: (a) a functional immunoglobulin heavy chain gene comprising, in operable linkage, a nucleic acid encoding an antibody heavy chain variable domain and a constant region coding sequence in which the IgY CH1 coding sequence is functionally deleted; and (b) a plurality of pseudogenes that are operably linked to said functional immunoglobulin heavy chain gene and that donate, by gene conversion, nucleotide sequence to the nucleic acid encoding the variable domain of (a), wherein the pseudogenes are upstream of the nucleic acid encoding an antibody heavy chain variable domain of (a).

6 Claims, 7 Drawing Sheets

Specification includes a Sequence Listing.

(56)      References Cited

OTHER PUBLICATIONS

Willis et al., "Human Germline Antibody Gene Segments Encode Polyspecific Antibodies", PLOS Computational Biology, 2013, 9(4): e1003045, pp. 1-14.

Kurosawa et al., "Genetic Diversification by Somatic Gene Conversion", Genes, 2011, 2: 48-58.

Mccormack et al., "Somatic Diversification of the Chicken Immunoglobulin Light-Chain Gene", Advances in Immunology, 1990, 48: 41-67.

Parvari et al., "Chicken immunoglobulin γ-heavy chains: limited VH gene repertoire, combinatorial diversification by D gene segments and evolution of the heavy chain locus", The EMBO Journal, 1988, 7(3): 739-744.

Reynaud et al., "A Hyperconversion Mechanism Generates the Chicken Light Chain Preimmune Repertoire", Cell, 1987, 48: 379-388.

Schusser et al., "Peer review correspondence, Expression of heavy chain-only antibodies can support B-cell development in light chain knockout chickens", European Journal of Immunology, 2016.

Adlersberg, "The Immunoglobulin Hinge (Interdomain) Region", La Ricerca Clin. Lab., 1976, 6(3):191-205.

Bahrami et al., "Designing A Transgenic Chicken: Applying New Approaches toward A Promising Bioreactor", Cell J., 2020, 22(2): 133-139.

Bednarczyk et al., "Generation of transgenic chickens by the non-viral, cell-based method: effectiveness of some elements of this strategy", Journal of Applied Genetics, 2018, 59: 81-89.

Bruggemann et al., "Heavy-Chain-Only Antibody Expression and B-Cell Development in the Mouse", Critical Reviews in Immunology, 2006, 26(5): 377-390.

Ching et al., "Chickens with humanized immunoglobulin genes generate antibodies with high affinity and broad epitope coverage to conserved targets", MABS, Jan. 2018, 10(1): 71-80.

Davey et al., "Illuminating the chicken model through genetic modification", Int. J. Dev. Biol., Jan. 2018, 62: 257-264.

Janssens et al., "Generation of heavy-chain-only antibodies in mice", PNAS, 2006, 103(41): 15130-15135.

Mallaby et al., "Diversification of immunoglobulin genes by gene conversion in the domestic chicken (*Gallus gallus domesticus*)", Discovery Immunology, 2023, 2, 1-12.

Nguyen et al., "Heavy-chain only antibodies derived from dromedary are secreted and displayed by mouse B cells", Immunology, 2003, 109: 93-101.

Ratcliffe, "Antibodies, immunoglobulin genes and the bursa of Fabricius in chicken B cell development", Developmental and Comparative Immunology, 2006, 30: 101-118.

Sayegh et al., "Efficient antibody diversification by gene conversion in vivo in the absence of selection for V(D)J-encoded determinants", The EMBO Journal, 1999, 18(22): 6319-6328.

Takeda et al., "RAG-2 expression is not essential for chicken immunoglobulin gene conversion", Proc. Natl. Acad. Sci., 1992, 89: 4023-4027.

Vidarsson et al., "IgG subclasses and allotypes: from structure to effector functions", Frontiers in Immunology, 2014, 5(520): 1-17.

Zou et al., "Expression of a Dromedary Heavy Chain-Only Antibody and B Cell Development in the Mouse", The Journal of Immunology, 2005, 175(6): 3769-3779.

* cited by examiner

All four IgY CH domains have short pseudo exons

| Guide name | Distance of cut from nearest HR in KO7 | Strand | Seq (PAM shown in lower case) |
|---|---|---|---|
| CH1gRNA1 | 11 bp, inside 3' HR | FWD | GGAGGTGCCGGGTAAGAGTG_cgg |
| CH1gRNA2 | 7 bp from 3' HR | FWD | GGGGGGCTGCTCAAAAAGG_agg |
| CH1gRNA3 | 61 bp from 3' HR | REV | GAAGCTTTTCCTCTTTCGC_cgg |
| CH1gRNA4 | 0 bp from 3' HR | FWD | CTGCTCAAAAGGAGGTGCC_ggg |
| CH1gRNA5 | 63 bp from 3' HR | REV | AGCTTTTCCTCTTCTGCCG_ggg |
| CH1gRNA6 | 176 bp from 5' HR, 107 bp from 3' HR | FWD | CGGTGACCGGCAGAGTTTCG_ggg |

FIG. 7

SEQUENCE LISTING

```
<160> NUMBER OF SEQ ID NOS: 10

<210> SEQ ID NO 1
<211> LENGTH: 815
<212> TYPE: DNA
<213> ORGANISM: Artificial sequence
<220> FEATURE:
<223> OTHER INFORMATION: synthetic sequence

<400> SEQUENCE: 1
ggtctctatg ggtctctatg gggctctatg gggcaggaga tgtccatcta tgggtctcta      60
tgggtctcta tggctctcta tggggcagga gcctgatctc tatgggtctc tatgggtctc     120
tatgggtctc tatgggtctc tatgaggcag gagcccggtc tctatgggtc tctatggggc     180
tctatgggtc tctatggggc aagagactca tctctatggg tctctatggg tctcaatggc     240
tctctatggg gctctatggg tctcaatgga gtcaagccta acccccccccc ctctccaccc     300 cacagcgggc cccacatcgc ccccccgcct gtacccattg tccgcctgtt gctcggactc     360
ggctgtcccg ccggccgtgg gctgcctgtt gtccccttcg tccgccggcg gcatctcctg     420
ggagggctcc ggaggtacgg cggtgaccgg cagagtttcg gggaccccccg tgaagctcag     480 cttcgtccgc ctcagccccg gcgagaagag gaaaagcttc gtctgcagcg ccgccccccgg     540 gggggcgctg ctcaaaaagg aggtgccggg taagagtgcg gggggggttg ggggggttgg     600
aggactcggg ggggggggttg gaggactcgg ggaggtcctc ctgtgggget gagaggggtt     660 gggggggggtt ggaggactcg gggggggggg gttggaggac tcggggggggg gttggaggac     720 tcggggaggt cctcctgtgg ggtttggggg agggttggag gtcctcctgt ggggctgaga     780
ggggttgggg ggggttgga ggtcctcctg tgggg                                  815

<210> SEQ ID NO 2
<211> LENGTH: 852
<212> TYPE: DNA
<213> ORGANISM: Artificial sequence
<220> FEATURE:
<223> OTHER INFORMATION: synthetic sequence

<400> SEQUENCE: 2
cgtctctatg ggtctctatg ggtctctatg ggtcatgaga ctcatctcta tgggtctcta      60
tggctctcta tgggtctcta tgggtctcta tgggtcaaga gactgatccc tatgggtctc     120
tatgggtctc tatgggtctc tatgggtcaa gagacttcaa tgtatgggtc aggagcccaa     180
tctctatggg tctctatggg tctctatggg tctctatggg tctcaatggc tctctatggg     240
```

-continued

```
tctctatggg gctctatggg gctctatggg gctctatgga tccctatggg gccaagccta       300
accccccccc cccttctcc cacccacag cgagccccac atcgccccc cgattgtacc          360 ctctatccgc ctgttgttcc gactcggctg tcccgccggc cgtgggctgc ctgttgtccc       420
cttcgtccgc cggcggcatc tcctgggagg gctccggagg tacggcggtg accggcagag       480
tttcggggac ccccgtgaag ctcagcttcg tccgcctcag ccccggcgag aagaggaaaa       540
gcttcgtctg cagcgccgcc cccgggggg cgctgctcaa aaaggaggtg ccgggtaaga        600
gtgggggggg ggtttggggg gggttggagg actcggggg gggttggagg actcggggag       660
gagctggggg gggggttagg gggggttgga ggactcgggg gggggggtt ggaggactcg        720 gggaggtcct cctgtggggc tgagaggggt tgggggggt tggaggtcct cctgtggggg       780 taagggggc gttggatgtc ctcctgtggg gctgagaggg gttggaggac tcggggaggt       840
cctcccgtgg gg                                                          852
```

<210> SEQ ID NO 3
<211> LENGTH: 1550
<212> TYPE: DNA
<213> ORGANISM: Artificial sequence
<220> FEATURE:
<223> OTHER INFORMATION: synthetic sequence

<400> SEQUENCE: 3

```
tcaagagact catctctatg ggtctctatg ggtctctatg ggtctctatg ggtcaagaga        60
ctcatctcta tgggtctcta tggggcagga gccccaaatc tatgcgtctc tatggggctc       120
tatgggtctc tatgggtctc tatgagccaa gagacacatc tctatgggtc tctatggagt       180
caagcctaac cctgtccccc tctcccaccc cacagcgagc cccacatctc cccccgcct        240 gtacccattg tccgcctgtt gctcggactc ggctgtcccc ccggccgtgg gctccctgtt       300
gtcttctgtg gggcacgagg gatctatggg cctctatggg gctctatggg tctctatgcg       360
tctcaatggc tctctatggg tctctatggg gtctctatgg gtctctatgg ggctctatgg      420
ggcaggagat gtccatctat gggtctctat gggtctctat ggctctctat ggggcaggag       480
cctgatctct atgggtctct atgggtctct atgggtctct atgggtctct atgaggcagg       540
agcccggtct ctatgggtct ctatggggct ctatgggtct ctatggggca agagactcat       600
ctctatgggt ctctatgggt ctcaatggct ctctatgggg ctctatgggt ctcaatggag       660
tcaagcctaa ccccccccc tctccacccc acagcgggcc ccacatcgcc ccccgcctg        720 tacccattgt ccgcctgttg ctcggactcg gctgtcccgc cggccgtggg ctgcctgttg      780
tccccttcgt ccgccggcgg catctcctgg gagggctccg gaggtacggc ggtgaccggc       840
agagtttcgg ggaccccgt gaagctcagc ttcgtccgcc tcagccccgg cgagaagagg        900
aaaagcttcg tctgcagcgc cgcccccggg ggggcgctgc tcaaaaagga ggtgccgggt       960
aagagtgcgg ggggggttgg ggggggttgga ggactcgggg ggggggttgg aggactcggg      1020
gaggtcctcc tgtggggctg agaggggttg ggggggggttg gaggactcgg ggggggggggg     1080 ttggaggact cggggggggg ttggaggact cggggaggtc ctcctgtggg gtttggggga      1140
gggttggagg tcctcctgtg gggctgagag gggttggggg ggggttggag gtcctcctgt       1200
ggggtttggg ggggtttggg ggcgttggag gacttggaga ggtcctcctg tggggctgag      1260
aggagttgga ggactcgggg aggtcctcct gtggggtttg gggaggttg gagggggttg       1320 gaggactcgg ggggggggt tggaggactc ggggggggggg gttggaggac tcggggaggt       1380
cctcctgtgg agctgaaagg ggttggggggg ggggttgggg ggggtttgga ggtcctcctg      1440
```

-continued

```
tggggtttgg ggggggttgg gggggggtttg gggggggttgg ggggggggttg ggggggggttg        1500 gaggactcgg ggaggtcctc ctgtgggggt aaggggggggt ttgggggggga                     1550
```

<210> SEQ ID NO 4
<211> LENGTH: 88
<212> TYPE: PRT
<213> ORGANISM: Artificial sequence
<220> FEATURE:
<223> OTHER INFORMATION: synthetic sequence

<400> SEQUENCE: 4

```
Ala Gly Pro Thr Ser Pro Pro Arg Leu Tyr Pro Leu Ser Ala Cys Cys
1               5                   10                  15

Ser Asp Ser Ala Val Pro Pro Ala Val Gly Cys Leu Leu Ser Pro Ser
            20                  25                  30

Ser Ala Gly Gly Ile Ser Trp Glu Gly Ser Gly Gly Thr Ala Val Thr
        35                  40                  45

Gly Arg Val Ser Gly Thr Pro Val Lys Leu Ser Phe Val Arg Leu Ser
    50                  55                  60

Pro Gly Glu Lys Arg Lys Ser Phe Val Cys Ser Ala Ala Pro Gly Gly
65                  70                  75                  80

Ala Leu Leu Lys Lys Glu Val Pro
                85
```

<210> SEQ ID NO 5
<211> LENGTH: 23
<212> TYPE: DNA
<213> ORGANISM: Artificial sequence
<220> FEATURE:
<223> OTHER INFORMATION: synthetic sequence

<400> SEQUENCE: 5

```
ggaggtgccg ggtaagagtg cgg                                                    23
```

<210> SEQ ID NO 6
<211> LENGTH: 23
<212> TYPE: DNA
<213> ORGANISM: Artificial sequence
<220> FEATURE:
<223> OTHER INFORMATION: synthetic sequence

<400> SEQUENCE: 6

```
gggggcgctg ctcaaaaagg agg                                                    23
```

<210> SEQ ID NO 7
<211> LENGTH: 23
<212> TYPE: DNA
<213> ORGANISM: Artificial sequence
<220> FEATURE:
<223> OTHER INFORMATION: synthetic sequence

<400> SEQUENCE: 7

```
gaagcttttc ctcttctcgc cgg                                                    23
```

<210> SEQ ID NO 8
<211> LENGTH: 23
<212> TYPE: DNA
<213> ORGANISM: Artificial sequence
<220> FEATURE:
<223> OTHER INFORMATION: synthetic sequence

<400> SEQUENCE: 8

-continued

```
ctgctcaaaa aggaggtgcc ggg                                              23

<210> SEQ ID NO 9
<211> LENGTH: 23
<212> TYPE: DNA
<213> ORGANISM: Artificial sequence
<220> FEATURE:
<223> OTHER INFORMATION: synthetic sequence

<400> SEQUENCE: 9
agcttttcct cttctcgccg ggg                                              23

<210> SEQ ID NO 10
<211> LENGTH: 23
<212> TYPE: DNA
<213> ORGANISM: Artificial sequence
<220> FEATURE:
<223> OTHER INFORMATION: synthetic sequence

<400> SEQUENCE: 10
cggtgaccgg cagagtttcg ggg                                              23
```

TRANSGENIC CHICKEN HAVING AN ENDOGENOUS IMMUNOGLOBULIN HEAVY CHAIN GENE IN WHICH THE IgY CH1 CODING SEQUENCE IS FUNCTIONALLY DELETED

CROSS-REFERENCING

This application is the national phase under 35 U.S.C. § 371 of International Application No. PCT/US2019/035535, filed on Jun. 5, 2019, which claims the benefit of U.S. provisional application Ser. No. 62/684,630, filed on Jun. 13, 2018, which applications are incorporated herein by reference.

BACKGROUND

Heavy chain-only antibodies can be expressed in the absence of light chain and therefore have what can be referred to as an autonomous heavy chain. An autonomous heavy chain variable domain (VH) can fold and bind to antigens autonomously, i.e., without aggregating and without the requirement of variable light chain (VL). Strategies for producing antibodies that comprise an autonomous heavy chain variable domain are reviewed in Janssens et al (Proc. Natl. Acad. Sci. 2006 103:15130-5), Brüggemann et al (Crit. Rev. Immunol. 2006 26:377-90), Zou et al (J. Immunol. 2005 175:3769-79) and Nguyen et al (Immunology 2003 109:93-101), for example.

The present disclosure relates to a way for making heavy-chain only antibodies in a chicken, by modifying the endogenous heavy chain locus and knocking out the light chain gene.

SUMMARY

Provided herein is a transgenic chicken comprising a genome having an endogenous immunoglobulin heavy chain gene in which the IgY CH1 coding sequence is functionally deleted. In certain embodiments, in B cells of the chicken the endogenous immunoglobulin heavy chain gene comprises: (a) a functional immunoglobulin heavy chain gene comprising, in operable linkage, a nucleic acid encoding an antibody heavy chain variable domain and a constant region coding sequence in which the IgY CH1 coding sequence is functionally deleted; and (b) a plurality of pseudogenes that are operably linked to the functional immunoglobulin heavy chain gene and that donate, by gene conversion, nucleotide sequence to the nucleic acid encoding the variable domain of (a), wherein the pseudogenes are upstream of the nucleic acid encoding an antibody heavy chain variable domain of (a).

In such animals, the nucleic acid encoding the heavy chain variable domain is diversified by gene conversion via the pseudogenes, to produce an IgY heavy chain that lacks a CH1 region. Because the IgY heavy chain lacks the CH1 region, it does not need to be paired with a light chain in order to bind its target. As such, the chicken produces a diversified population of autonomous heavy chain antibodies that have undergone clonal selection by the chicken's own immune system.

BRIEF DESCRIPTION OF THE DRAWINGS

The skilled artisan will understand that the drawings, described below, are for illustration purposes only. The drawings are not intended to limit the scope of the present teachings in any way.

FIG. 7 provides the sequences and positions of 6 gRNAs designed to direct cutting in the chicken IgY CH1 exon. SEQ ID NOS. 5-10.

Definitions

Figure 1:
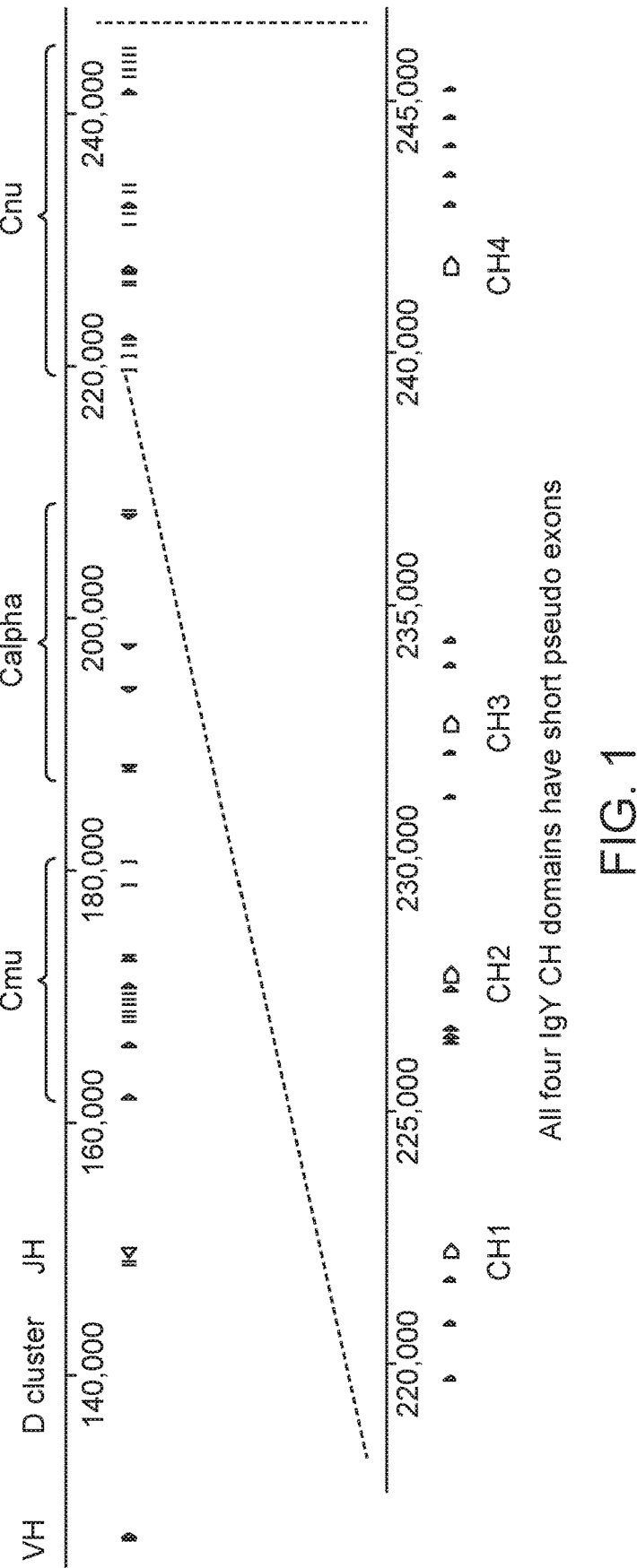
FIG. 1 schematically illustrates a map of chicken IgH locus, as determined using Oxford Nanopore sequencing. The top line shows the locus from the functional VH to the end of Cnu. The VH pseudogenes are not shown, but are found to the left of the diagram upstream of the functional VH. Each constant region gene, Cmu (encoding IgM), Calpha (encoding IgA) and Cnu (encoding IgY) contains four exons, encoding the four CH domains in each isotype, and a number of short related sequences ("pseudo exons"). The pseudo exons are ~50-90 bp in length (compared to ~300 bp for each coding exon) and are sequences related to the 5' or 3' ends of the coding exon that is closest to it. Below is an expanded view of the Cnu gene, spread over ~26 kb of genomic DNA. The coding exons are as indicated, and the pseudo exons are the smaller arrows upstream and/or downstream of the coding exons.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of"

includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. "Unlinked" means that the associated genetic elements are not closely associated with one another and the function of one does not affect the other.

The term "homozygous" indicates that identical alleles reside at the same loci on homologous chromosomes. In contrast, "heterozygous" indicates that different alleles reside at the same loci on homologous chromosomes. A transgenic animal may be homozygous for a transgene, or hemizygous for a transgene if there is no counterpart at the same locus on the homologous chromosome.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introducing" in the context of inserting a nucleic acid sequence into a cell, includes "transfection" and "transformation" and all other methods of introducing a nucleic acid into a cell, where the nucleic acid sequence may be incorporated into the genome of the cell (e.g., chromosome, plasmid, plastid, or mitochondrial DNA) or converted into an autonomous replicon, or transiently expressed.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The term "replacing", in the context of replacing one genetic locus with another, refers to a single step protocol or multiple step protocol.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "isolated", with respect to a cell, refers to a cell that is cultured in vitro. If an animal is described as containing isolated cells, then those isolated cells were cultured in vitro and then implanted into the animal.

The term "progeny" or "off-spring" refers to any and all future generations derived and descending from a particular animal or cell. Thus, the progeny an animal of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell. A chimeric animal may have cells donated by another animal in the germline, in which case the progeny of the animal may be heterozygous for chromosomes in the donated cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The phrases "hybrid animal", "transgenic hybrid animal" and the like are used interchangeably herein to mean an animal obtained from the mating of a first animal having certain qualities with a second animal having certain qualities. For example, a hybrid animal of the present disclosure can refer to the transgenic progeny obtained from the mating of a transgenic first animal that produces a common light-chain with a second transgenic animal that produces a synthetic heavy-chain. A hybrid animal can be immunized and used as a source for the production of antigen-specific antibodies.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab') 2, and or other antibody fragments that retain specific binding to antigen, and monoclonal antibodies.

Antibodies may exist in a variety of other forms including, for example, Fv, Fab, and (Fab') 2, as well as bifunctional (i.e. bispecific) hybrid antibodies (e.g., Lanzavecchia and Scheidegger, Eur. J. Immunol. 1987, 17 (1): 105-111) and in single chains (e.g., Huston et al., Proc. Natl. Acad. Sci. U.S.A 1988, 85 (16): 5879-5883 and Bird et al., Science. 1988, 242 (4877): 423-426, which are incorporated herein by reference). (See, generally, Hood et al., "Immunology", Benjamin, N.Y., 2nd ed. 1984, and Hunkapiller and Hood, Nature. 1986, 323 (6083): 15-16).

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. In the context of the heavy and light chain immunoglobulin loci, pseudogenes do not contain promoter regions, recombination signal sequences or leader sequences.

The terms "upstream" and "downstream" are used with reference to the direction of transcription.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and analyte when they are specifically bound in an antibody/analyte complex is characterized by a KD (dissociation constant) of less than 10-6 M, less than 10-7 M, less than 10-8 M, less than 10-9 M, less than 10-9 M, less than 10-11 M, or less than about 10-12 M or less.

A "variable region" of a heavy or light antibody chain is an N-terminal mature domain of the chain that contains CDR1, CDR2 and CD3, and framework regions (where CDR refers to "complementarity determining region"). The heavy and light chain of an antibody both contains a variable domain. All domains, CDRs and residue numbers are assigned on the basis of sequence alignments and structural knowledge. Identification and numbering of framework and CDR residues is as described in by Chothia et al. and others (Chotia et al., J. Mol. Biol. 1998, 278 (2): 457-479).

VH is the variable domain of an antibody heavy chain. VL is the variable domain of an antibody light chain.

The terms "gene" and "locus" are used interchangeably herein. Neither term implies that a gene is actively transcribed or intact. Both terms encompass genes that have been inactivated.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "genetically linked" refers to two genetic elements that exist on the same chromosome such that there is a tendency for the genetic elements to be inherited together during meiosis (i.e., the elements have a recombination frequency of less than 50%, less than 40%, less than 30%, less than 20%, less than 10% or less than 5%). Two genetic elements that are linked closely to each other are less likely to be separated onto different chromatids during chromosomal crossover events (or "recombination"). The chance that two genetically linked elements become separated during recombination depends on the amount of sequence between the two elements, and can be calculated into a percentage of likelihood, termed "recombination frequency".

The term "autonomous heavy chain variable domain" refers to a heavy chain variable domain that can fold and bind to epitopes autonomously, i.e., without aggregating and or an associated light chain. "Heavy chain-only" or "HCO" antibodies, shark antibodies, VHH antibodies, camilids, and single domain antibodies are all examples of antibodies that contain an autonomous heavy chain variable domain. Several strategies for producing such antibodies are reviewed in Janssens et al (Proc. Natl. Acad. Sci. 2006 103:15130-5), Brüggemann et al (Crit. Rev. Immunol. 2006 26:377-90), Zou et al (J. Immunol. 2005 175:3769-79) and Nguyen et al (Immunology 2003 109:93-101), for example. An autonomous heavy chain variable domain can be made by introducing camelizing substitutions into the variable domain of a VH antibody.

As used herein, the term "functional" is intended to mean that the region is transcribed and translated by the cell.

Further definitions may be found elsewhere in this disclosure.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a". "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to ante-date such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a transgenic animal is provided. In certain embodiments, the animal may be any non-human animal that has a relatively small number of light chain genes, or an animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagamorph such as rabbit, or a farm animal such as a cow, sheep, pig or goat.

Some of this disclosure relates to a transgenic chicken containing one or more transgenes. Since the nucleotide sequences of the immunoglobulin loci of many animals are known, as are methods for modifying the genome of such animals, the general concepts described below may be readily adapted to any suitable animal, particularly animals that employ gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17:43-70), Buc-chini (Nature 1987 326:409-11), Knight (Adv. Immunol. 1994 56:179-218), Langman (Res. Immunol. 1993 144:422-46), Masteller (Int. Rev. Immunol. 1997 15:185-206), Reynaud (Cell 1989 59:171-83) and Ratcliffe (Dev. Comp. Immunol. 2006 30:101-118). See also US20110055938.

As noted above, a transgenic chicken comprising a genome having an endogenous immunoglobulin heavy chain gene in which the IgY CH1 coding sequence is functionally deleted is provided. In some embodiments, in B cells of the chicken the endogenous immunoglobulin heavy chain gene comprises: (a) a functional immunoglobulin heavy chain gene comprising, in operable linkage, a nucleic acid encoding an antibody heavy chain variable domain and a constant region coding sequence in which the IgY CH1 coding sequence is functionally deleted; and (b) a plurality of pseudogenes that are operably linked to said functional immunoglobulin heavy chain gene and that donate, by gene conversion, nucleotide sequence to the nucleic acid encoding the variable domain of (a), wherein the pseudogenes are upstream of the nucleic acid encoding an antibody heavy chain variable domain of (a). The pseudogenes diversify the variable domain by gene conversion.

In some embodiments, the antibody heavy chain variable domain of (a) is an autonomous heavy chain (AHC) variable domain. Typical "natural" antibodies from humans and mice are composed of a heavy chain and a light chain. In the absence of the light chain, the heavy chains of these anti-bodies do not fold properly and they aggregate. "Cameliza-tion" refers to a process by which VH domains (which term describes the type of binding domain from humans and mice IgGs) are altered so that they are capable of binding to epitopes on their own (i.e., without light chain) and do not aggregate. The term "camelization" has been coined for this process because camelids (e.g., camels, llamas, etc.) produce functional antibodies devoid of light chains of which the single N-terminal domain (VHH) is fully capable of antigen binding. These autonomous heavy chain antibodies have a high stability and solubility. Sharks and other cartilaginous fish also VHH antibodies.

Similar to conventional VH domains, autonomous heavy chain antibodies contain four framework regions (FRs) that form the core structure of the immunoglobulin domain and three complementarity-determining regions (CDRs) that are involved in antigen binding. Sec, e.g.,, Conrath et al., Antigen binding and solubility effects upon the veneering of a camel VHH in framework-2 to mimic a VH, J Mol Biol, 2005, 350:112-25. Sequence comparison of human and camelid variable domains led to the process of camelization, which involves the transfer of a few hallmark residues of aggregation-resistant VHH domains to human VH domains. See, e.g., Davies et al., 'Camelising' human antibody frag-ments: NMR studies on VH domains, FEBS Lett, 1994, 339:285-90. For example, a characteristic feature of VHHs is the presence of amino acid substitutions at four FR2 positions (positions 37, 44, 45, and 47; Kabat numbering) that are conserved in conventional VH domains and that are involved in forming the hydrophobic interface with VL domains. Specifically, the sequence of the camelid FR's and that of the human VH3 family were remarkably similar except for three residues (44, 45 and 47) in FR2, of which is usually highly conserved in VH domains. See, e.g., Conrath et al., 2005. These solvent-exposed residues (most of which are hydrophilic in the camelids) are located in the former light chain interface and impede the association with a VL domain. Non-specific binding of VH by its interface for the light chain variable domain (VL) has prevented through amino acid mutations in framework 2 and 4 (Val37F, G44E, L45R, W47G and W103R). See Da Silva et al, Camelized rabbit-derived VH single-domain intrabodies against Vif strongly neutralize HIV-1 infectivity J Mol Biol. 2004 Jul. 9; 340 (3): 525-42. Other strategies for camelization are described in Tanha et al Protein Eng Des Sel. 2006 Improv-ing solubility and refolding efficiency of human V(H) s by a novel mutational approach Nov; 19 (11): 503-9 and Davies et al Single antibody domains as small recognition units: design and in vitro antigen selection of camelized, human VH domains with improved protein stability. Protein Eng. 1996 June; 9 (6): 531-7.

Analogous mutational approaches to humanize VHHs have also been attempted. See, e.g., Conrath et al., 2005. See also Vincke et al., General strategy to humanize a camelid single-domain antibody and identification of a universal humanized nanobody scaffold, J Biol Chem, 2009, 284: 3273-84. Although the increased hydrophilicity of VHHs predominantly relies on the aforementioned changes in the former VL interface, some amino acids at positions that form a slightly hydrophobic patch on conventional VH domains that contacts the CH1 domain are also changed into hydro-philic residues in VHHs. Sec, e.g., Lesk et al., Elbow motion in the immunoglobulins involves a molecular ball-and-socket joint, Nature, 1988 Sep. 8, 335 (6186): 188-90. See also Muyldermans et al., Sequence and structure of VH domain from naturally occurring camel heavy chain immu-noglobulins lacking light chains, Protein Eng, 1994 Sep. 7 (9): 1129-35.

As such, in some embodiments any VH antibody may be camelized by making camelizing amino acid substitutions of any hydrophobic residues at one or more of positions 37, 44, 45, and 47 in the FR2 and, optionally, position 103 of FR4 to a non-hydrophobic residue (Kabat numbering). A camelizing amino acid substitutions may include substitution of any hydrophobic residues glycine (Gly), alanine (Ala), valine (Val), leucine (Leu), isoleucine (Ile), proline (Pro), phenylalanine (Phe), methionine (Met), and tryptophan (Trp) at the one or more positions with a non-hydrophobic residue.

Heavy chain-only antibodies have what is referred to as an autonomous heavy chain variable domain, i.e., a heavy chain variable domain that can fold and bind to epitopes autonomously, i.e., without aggregating and or an associated light chain. Strategies for producing antibodies that comprise an autonomous heavy chain variable domain are reviewed in Janssens et al (Proc. Natl. Acad. Sci. 2006 103:15130-5), Brüggemann et al (Crit. Rev. Immunol. 2006 26:377-90), Zou et al (J. Immunol. 2005 175:3769-79) and Nguyen et al (Immunology 2003 109: 93-101), for example.

In some embodiments, the autonomous heavy chain variable domain of (a) is a camelized human heavy chain variable domain.

In some embodiments, the pseudogenes of (b) encode human germline antibody sequences. In some embodiments, the antibody heavy chain variable domain of (a) is a human heavy chain variable domain and the pseudogenes of (b) introduce camelizing mutations into the human heavy chain variable domain via gene conversion. In these embodiments, the antibody heavy chain variable domain may be from a human monoclonal antibody, with the optional exception of up to 10 camelizing amino acid substitutions.

For example, in any embodiment, the pseudogenes and/or the functional gene may encode variable domains having non-hydrophobic residues at one, two, three, four or all five amino acid positions 37, 44, 45, and 47 in the FR2 and, optionally, position 103 of FR4. In some embodiments, all pseudogenes have non-hydrophobic residues at three or four positions selected from positions 37, 44, 45, and 47 (Kabat numbering).

In some embodiments, the antibody heavy chain variable domain (a) may be encoded by a human germline heavy chain V segment, a human germline heavy chain D segment and a human germline heavy chain J segment, with the optional exception of up to 10 camelizing amino acid substitutions.

In some embodiments, the IgM CH1 coding sequence is also functionally deleted in the endogenous immunoglobulin heavy chain gene of (a). The IgM CH1 coding sequence need not be deleted in the chicken because chickens are believed to produce a detectable amount of antigen-specific heavy chain antibody in which the CH1 region has been deleted spontaneously. These IgM heavy chains, which are believed to be autonomous because they do not have a CH1 region and therefore cannot bind to a light chain, are believed to be in sufficient abundance to initiate class switching (from IgM to IgY) based on binding of the IgM antibodies to the target antigen.

The IgY CH1 coding sequence can be functionally deleted in a variety of different ways. For example, one can simply remove at least some of the IgY CH1 coding sequence in frame, by removing at least 50% of the IgY CH1 coding sequence, at least 70% of the IgY CH1 coding sequence, at least 90% of the IgY CH1 coding sequence or all of the IgY CH1 coding sequence from the IgY constant region coding sequence. Alternatively or in combination, one could mutate the cysteine codons and the codons for amino acids that interact with the light chain, thereby destroying the ability of the IgY CH1 region to interact with the light chain.

In some embodiments, the animal may have a functionally deleted immunoglobulin light chain locus, e.g., a knocked out light chain locus that produces no light chain.

In many embodiments, the chicken may make autonomous heavy chain variable domain antibodies.

In any embodiment, the transgenic chicken can be homozygous or heterozygous for the locus.

In some embodiments, the sequences that encode FR1. FR2 and FR3 and, optionally FR4, if present, in the pseudogenes of (b) are, combined, at least 90% identical to the combined sequences that encode the corresponding FR1. FR2 and FR3 and, optionally FR4 in the variable domain of (a). For each individual FR in the pseudogenes, the level of sequence identity may be at least 80%, e.g., at least 90% or at least 95% in many cases. In some embodiments, the sequences that encode the CDRs in the pseudogenes of (b) are no more than 90% identical to the sequences that encode the corresponding CDRs in the variable domain of (a). In other words, in some embodiments there may be more diversity in the CDRs encoded by the pseudogenes relative to the FW sequences encoded by the pseudogenes.

In some embodiments, the endogenous the endogenous immunoglobulin heavy chain gene in which the IgY CH1 coding sequence is functionally deleted may be further modified to contain a sequence that encodes a hinge. In these embodiments, the hinge coding sequence can be added to the coding sequence of the C-terminal end of the antibody heavy chain variable domain (i.e., after the FW4 coding sequence but before the intron) or, alternatively at the beginning of the coding sequence of the CH2 region of the IgY heavy chain such that the heavy chain has the formula V—H—C, where V is the variable region, H is the hinge and C is a CH1 IgY constant region. In some embodiments, the hinge can be a human hinge, the core sequences for which (e.g., CPPCP) are well known or, alternatively, the hinge can be a flexible linker (e.g., a linker made up of 2-10 Gly and/and Ser residues) for example.

Also provided is a method comprising (a) immunizing a transgenic animal with an antigen; and (b) obtaining from said animal an antibody that specifically binds to said antigen. The antibody may be polyclonal or monoclonal. In these embodiments, the method may further comprise (c) making hybridomas using B cells of the transgenic animal; and (d) screening said hybridomas to identify a hybridoma that produces an antibody that specifically binds to the antigen. Alternatively, the method may comprise (c) screening B cells without making hybridomas to identify a B cell that produces an antibody that specifically binds to the antigen. In any screening method, the method may involve using PCR to amplify at least the heavy chain variable region-encoding nucleic acid from B cells of the transgenic animal, and expressing a recombinant antibody using said amplified nucleic acid.

A monoclonal or polyclonal antibody produced by the transgenic animal is also provided, wherein the antibody is an autonomous heavy chain (AHC) variable domain antibody.

Also provided is a B cell isolated from the animal.

The transgenic animal contains a functional immunoglobulin heavy chain gene that is expressed (i.e., transcribed to produce an mRNA that is subsequently translated) to produce a heavy chain of an antibody, and, operably linked to (which, in the case in chicken and many other species is immediately upstream of) the functional heavy chain gene, a plurality of different pseudogene heavy chain variable regions, where the variable regions of the pseudogenes are operably linked to the functional immunoglobulin heavy chain in that they the alter the sequence of the functional immunoglobulin heavy chain gene by gene conversion (i.e., by substituting a sequence of the functional immunoglobulin heavy chain gene variable region with a sequence of a pseudogene variable region). In the transgenic animal, gene conversion between the functional immunoglobulin heavy chain gene variable region and a pseudogene variable region alters the sequence of the functional immunoglobulin heavy chain gene variable region by as little as a single codon up to the entire length of the variable region. In certain cases a pseudogene variable region may donate the sequence of at least one CDR (e.g., CDR1, CDR2 or CDR3) from a pseudogene variable region in to the variable region of the functional gene. The heavy chains of the antibodies produced by the transgenic animal are therefore encoded by whatever sequence is donated from the pseudogene variable regions into the variable region of the functional heavy chain gene. Since different sequences are donated in different cells of the animal, the antibody repertoire of the animal is determined by which sequences are donated from the pseudogene variable regions to the variable region of the functional gene.

In some embodiments, the framework segments of the human functional gene and the pseudogenes may be identical or near identical to one another, while the CDR segments of the functional gene and the pseudogenes may differ, thereby allowing gene conversion to occur between the CDR segments of the pseudogenes and the germline sequence. Further, the CDRs may vary in length. In certain embodiments, the heavy chain CDR1 may be in the range of 6 to 12 amino acid residues in length, the heavy chain CDR2 may be in the range of 4 to 12 amino acid residues in length, the heavy chain CDR3 may be in the range of 3 to 25 amino acid residues in length, although antibodies having CDRs of lengths outside of these ranges are envisioned.

In some embodiments, the nucleotide sequence and/or amino acid sequence of the introduced transcribed variable region may be human, i.e., may contain the nucleotide and/or amino acid sequence of a human antibody or germline sequence. In these embodiments, both the CDRs and the framework may be human. In other embodiments, the nucleotide sequence and/or amino acid sequence of the introduced transcribed variable region is not human and may instead be at least 80% identical, at least 90% identical, at least 95% or more identical to a human sequence. For example, relative to a human sequence, the introduced transcribed variable region may contain one or more nucleotide or amino acid substitution. Any germline human VH segments may be the selected from the following sequences: VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In some embodiments, part of the heavy chain locus, including the constant region, part of an intron region and the 3'UTR of the functional gene, may be endogenous to the animal and the remainder of the heavy chain locus, including the variable domains of the functional gene, the remainder of the intron and the pseudogenes may be exogenous to the animal, i.e., made recombinantly and introduced into the animal proximal to the constant domain, part intron and 3' UTR in such a way that a functional gene is produced and the pseudogenes are capable of donating sequence to the functional gene by gene conversion. In certain cases the heavy chain locus of the animal may contain, in operable linkage: an intron region, a constant domain-encoding region and a 3' untranslated region, where the intron region, the constant domain-encoding region and the 3' untranslated region are endogenous to the genome of the transgenic animal, and a plurality of pseudogene heavy chain variable regions, where the plurality of pseudogene heavy chain variable regions are exogenous to the genome of the transgenic animal.

In certain embodiments, an antibody produced by a subject transgenic animal may contain an endogenous constant domain and variable domains that are exogenous to the animal. Since an endogenous constant region may be employed in these embodiments, the antibody may still undergo class switching and affinity maturation, which allows the animal to undergo normal immune system development, and mount normal immune responses. In specific embodiments transgenic chickens have three endogenous constant regions in the heavy chain locus encoding IgM, IgY and IgA. During the early stages of B cell development, B cells express IgM. As affinity maturation proceeds, class switching converts the constant region into IgY or IgA. IgY provides humoral immunity to both adults and neonatal chicks which receive about 200 mg of IgY via a reserve deposited into egg yolk. IgA is found primarily in lymphoid tissues (eg. the spleen, Peyer's patches and Harderian glands) and in the oviduct.

The number of introduced pseudogene variable regions present at the light and/or heavy chain locus may vary and, in particular embodiments, may be in the range of 1-50, e.g., 2 to 50 or 10 to 25. In particular embodiments, at least one (e.g., at least 2, at least 3, at least 5, at least 10 or more) of the plurality of pseudogene light chain variable regions may be in reverse orientation relative to the transcribed light chain variable region. Likewise, in particular embodiments, at least one (e.g., at least 2, at least 3, at least 5, at least 10 or more) of the plurality of pseudogene heavy chain variable regions may be in reverse orientation relative to the heavy chain transcribed variable region. In particular embodiments, the plurality of pseudogene variable regions are not in alternating orientations, and in certain cases may contain a series of at least 5 or at least 10 adjacent pseudogene regions that are in opposite orientation relative to the transcribed variable region. In one embodiment, the pseudogene region that is most distal from the transcribed variable region is in the same orientation as the transcribed variable region, and the pseudogene regions between the most distal region and the transcribed variable region are in the reverse orientation relative to the transcribed variable region.

A pseudogene typically contains a sequence of at least 50, at least 100, at least 200 or at least 300 contiguous nucleotides that is at least 80% identical, e.g., at least 85% identical, at least 90% identical or at least 895% identical to sequence in the transcribed region. In some embodiments, the framework sequences in the pseudogene are at least 90% identical to corresponding framework sequences in the functional gene, and the CDRs have less sequence identity.

The above-described transgenic animal may be made by modifying the genome of an animal recombinantly. Methods for producing transgenic animals, e.g., mice and chickens, etc. are known, and, in particular, methods for modifying the genomes of animal that use gene conversion are also known (see, e.g., Sayegh, Vet. Immunol. Immunopathol. 1999 72:31-7 and Kamihira, Adv. Biochem. Eng. Biotechnol. 2004 91:171-89 for birds, and Bosze, Transgenic Res. 2003 12:541-53 and Fan, Pathol. Int. 1999 49:583-94 for rabbits and Salamone J. Biotechnol. 2006 124:469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30:101-118), the above-described animal may be made by routine methods given this disclosure. Methods for making transgenic chickens are known. See, e.g., 8,592,644, U.S. Pat. No. 8,889,662, Collarini et al (Poult Sci. 2015 94:799-803), van de Lavoir (Nature. 2006 441:766-9) and Schusser et al (Proc Natl Acad Sci USA. 2013 110:20170-5.

Also provided is a method for producing antibodies that contain an autonomous heavy chain (AHC) variable domain. In some embodiments this method may comprise: immunizing a transgenic animal as described above with antigen, and, if the antibodies are polyclonal, the method may comprise isolating the antibodies from a bleed from the animal. If the animal is homozygous for the common light chain sequence, then all of the antibodies in the polyclonal antisera should be autonomous heavy chain (AHC) variable domain antibodies. If monoclonal antibodies are desired, then the method may comprise b) making hybridomas using cells of the immunized transgenic animal; c) screening the hybridomas to identify an antigen-specific hybridoma; and d) isolating an antigen-specific antibody from the antigen-specific hybridoma. Alternatively, B cells can be screened.

In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL-related ligand), CA125 (carcinoma antigen 125), CEA (carcinoembryonic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, cotaxin (cytokine A11), HER2/neu, HER3, HLA-DR, HLA-DR10, HLA ClassII, IgE, GPiib/iiia (integrin), Integrin aVβ3, Integrins a4β1 and a4β7, Integrin β2, IFN-gamma, IL-1B, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFBR (Beta platelet-derived growth factor receptor), PMSA, renal carcinoma antigen G250, RSV, E-Selectin, TGFbeta1, TGF-beta2, TNFα, DR4, DR5, DR6, VAP-1 (vascular adhesion protein 1) or VEGF, or the like in order to produce a therapeutic antibody.

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, antibody-producing cells, e.g., spleen cells, may isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al.,. J Immunol Methods 242:159 (2000), and by Burton, Immunotechnology 1:87 (1995), the disclosures of which are incorporated herein by reference.

If the antibody does not already contain human framework regions, the method may further include humanizing the antibody, which method may include swapping the constant domain of the antibody with a human constant domain to make a chimeric antibody, as well as in certain cases humanizing the variable domains of the antibody by e.g., CDR grafting or resurfacing etc. Humanization can be done following the method of Winter (Jones et al., Nature 321:522 (1986); Riechmann et al., Nature 332:323 (1988); Verhocyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including references cited therein.

As such, in addition to the transgenic animal, a method comprising immunizing the transgenic animal with an antigen and obtaining from the transgenic animal an antibody that specifically binds to the antigen is also provided. The method may include making hybridomas using cells of the transgenic animal; and screening the hybridomas to identify a hybridoma that produces an antibody that specifically binds to the antigen. Alternatively B cells can be screened without making hybridomas.

The heavy chains variable domain of the antibodies are made "naturally" by the immune system of the animal. Such antibodies may, in certain case, be post-translationally modified (e.g., glycosylated) by the host cell and may have a glycosylation pattern and composition characteristic of the species of transgenic animal.

The sequences of the antigen-specific binding regions of antibodies produced by the transgenic animal described above should be relatively straightforward to obtain because, if desired, all or any of the coding sequences for a diversified population of heavy chain variable domains can be amplified from cDNA using a single pair of PCR primers. Because the specificity and affinity of each antibody should be solely determined by the amino acid sequence of the heavy chain variable domain, there is no need to identify or sequence the cognate light chain. As such, the amino acid sequences for antigen-specific heavy chain variable domains should be relatively straightforward to obtain. As noted above, in some cases, B cells or hybridomas may be functionally screened in order to select for cells that express antigen-specific heavy chains. Heavy chain variable domain coding sequences may be amplified from an enriched or unenriched population of B cells (e.g., PBMCs) en masse. If sequences are amplified from an unenriched population of B cells, the sequences encoding antigen-specific variable domains should be identifiable because they are more highly expressed than sequences that are not antigen-specific (due to B cell activation) and because they potentially belong to more variable clades. Moreover, because these heavy chains do not need a specific light chain for binding, there is no need to determine which light chain pairs with which heavy chain before performing follow up work.

EXAMPLES

The following examples are provided in order to demonstrate and further illustrate certain embodiments and aspects of the present invention and are not to be construed as limiting the scope thereof.

Example 1

Construction of CH1-CHickens

To delete the sequence encoding the IgY CH1 domain, the genomic sequence surrounding the CH1 coding sequence should be known in order to design a targeting vector. In chicken primordial germ cells (PGCs), it is important that targeting vectors contain homology regions that are isogenic to the targeted locus. As such, unless the sequence is known it would be impossible to successfully perform this work. PGC line (1783-10) was used. This line has been previously targeted twice at the heavy chain locus for humanization of the variable region-encoding genes. One of the previous modifications was to delete the chicken JH segment and replace it with a promoterless neo and an attP site. The attP-neo cassette was placed in the chicken IgH locus for site-specific integration of constructs encoding human immunoglobulin variable region sequences into the chicken genome. The second modification was to insert a loxP site upstream of the functional chicken VH gene, to delete the chicken V and D genes with Cre. Since these are the cells we will be using for the IgY CH1 deletion, they were used for genomic sequencing of the IgY CH region.

Several approaches were to determine the genomic sequence surrounding IgY CH1 in the 1783-10 PGC line. First, Oxford Nanopore long-read sequencing technology was used to do a de novo genome assembly. The Oxford Nanopore genome assembly was able to provide a general structure for the entire locus, but the sequence quality was too low to be able to design a targeting vector for the CH1 exon. The locus was found to span approximately 162 kb, from the most 5' VH pseudogene to the end of the IgY constant region locus. The order of genes in the locus was confirmed as pseudo VH-functional VH-D-JH-Cmu-Calpha-Cnu (although the JH gene was replaced with attP-neo, which was found in the assembly). The Calpha locus is inverted relative to the rest of the genes. Each constant region is encoded in 4 exons, one exon for each constant region protein domain, spread over about 20-25 kb for each isotype. The introns between the CH domain exons are much longer than those found in humans (4-5 kb in chicken vs. less than 1 kb for most of the introns in humans). Closer inspection of the intronic sequences revealed that they contain short sections of sequence related to the CH coding sequences. We have called these short CH-related sequences "pseudo exons". The pseudo exons are ~50-90 bp in length (compared to ~300 bp for each coding exon) and are sequences related to the 5' or 3' ends of the coding exon that is closest to it. The number of pseudo exons near each CH exon varies and they can be either 5' or 3' of the coding exon that they are related to. They were found predominantly in the introns of Cmu and Cnu and to a lesser extent in Calpha. These types of pseudo exons are not found in the human or duck IgH loci. These pseudo exons impact the design of the targeting strategy, as described below. A map of the chicken IgH locus, as determined using Oxford Nanopore sequencing, is shown in FIG. 1.

Figure 2:
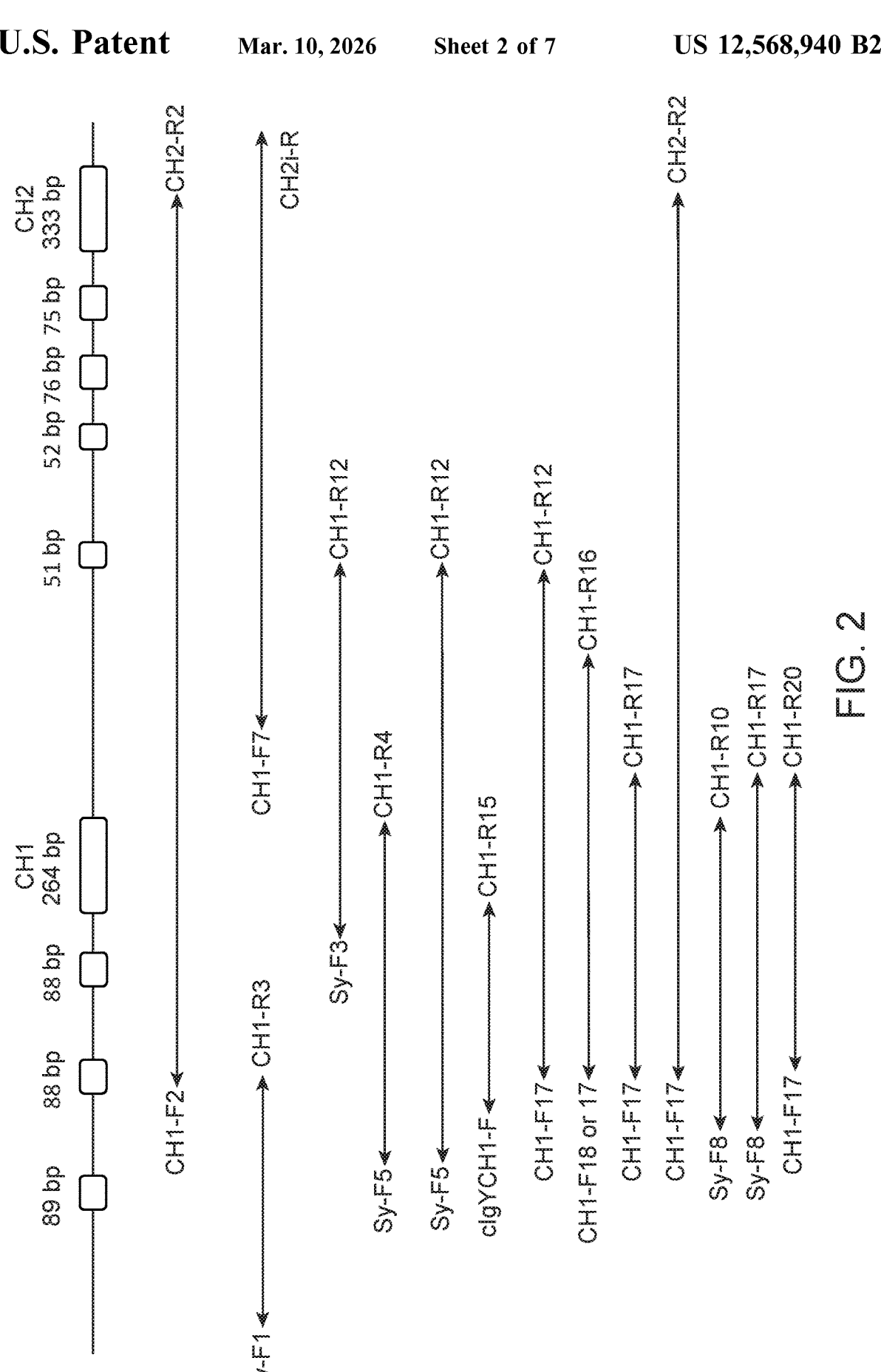
FIG. 2 shows the strategy for sequencing PCR products around CH1 region. The CH1 and CH2 coding exons as well as the pseudo exons are shown, with their sizes. The PCR products that were cloned and sequenced are shown below the diagram of the CH1-CH2 region.
Figure 3:
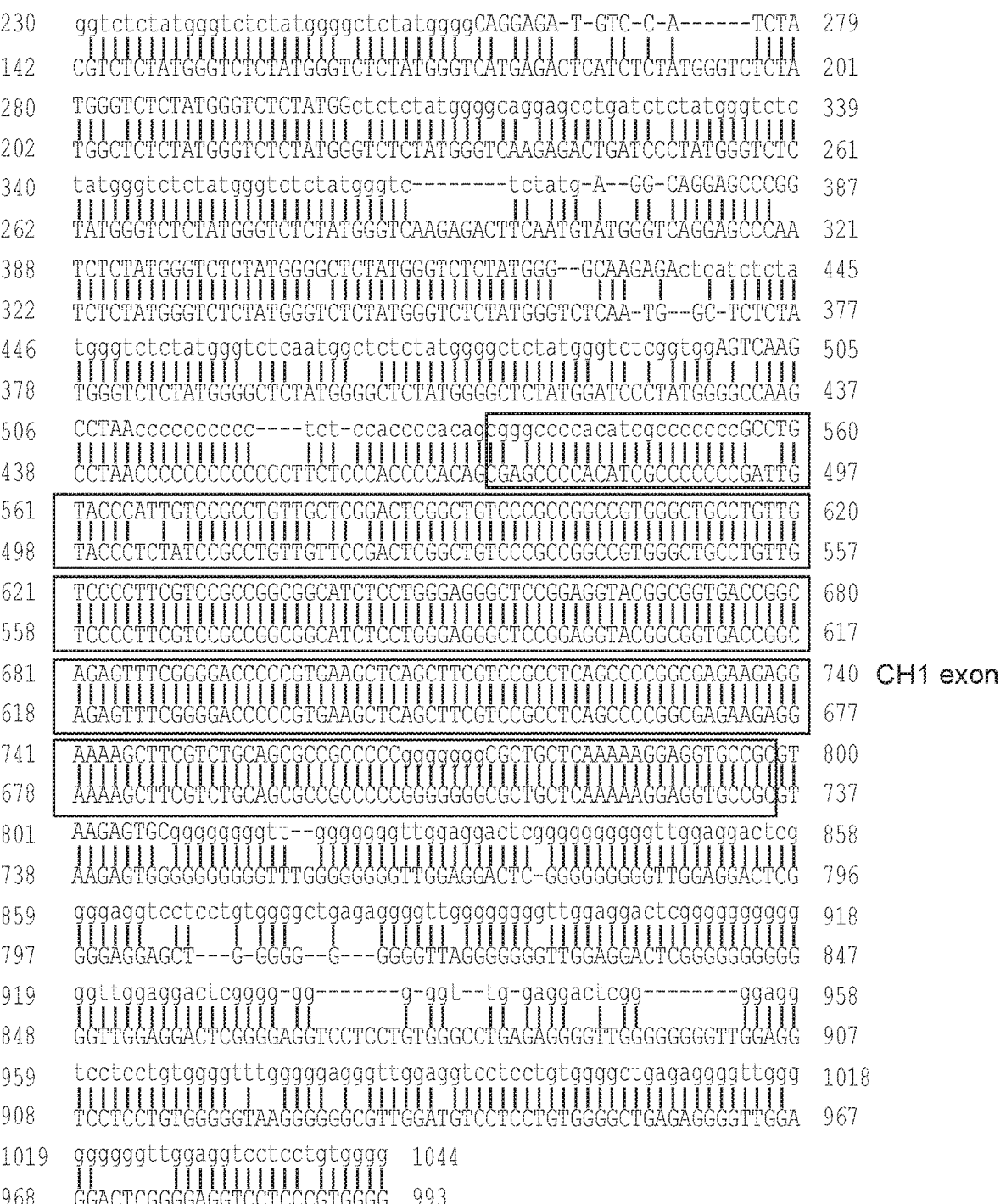
FIG. 3 shows an alignment of the two alleles of the IgY CH1 genomic region in the PGC cell line used for targeting. The CH1 coding exon is boxed. The two alleles are seen to be highly polymorphic between the two alleles in the upstream and downstream flanking regions. The upstream region represents the switch region used in class switch recombination. The downstream region contains many homopolymeric G tracts. SEQ ID NOS. 1 and 2.

To determine the exact nucleotide sequence of the region surrounding the IgY CH1 exon, PCR primers were designed in the CH1 and CH2 coding sequences that were known from sequencing cDNAs from the transgenic birds, and in the regions upstream and downstream of CH1, using sequence from the public databases. PCR was performed on gDNA from the 1783-10 cells which will be used for the IgY CH1 targeting, in order to determine the isogenic DNA sequence from the allele that we would like to target. The PCR strategy is shown in FIG. 2. The CH1 deletion should occur on the same chromosome as the human VHH insertion (which has a camelized human VH region). The VHH insertion and CH1 deletion will be performed by sequential transfection in the PGCs, and in order for the heavy chain only antibodies to be expressed, the VHH insertion and CH1 deletion must reside on the same chromosome. Previously, we had produced transgenic birds from inserting a human heavy chain variable region into the attP site of 1783-10, and we sequenced IgH cDNAs obtained from this bird. The sequence of the CH1 exon that is spliced to the human VH was determined. We then looked for this CH1 sequence in the genomic DNA from the cells. A number of PCR products were cloned and sequenced. The previously identified CH1 sequence was obtained, as well as the presumptive other allele. The two alleles differ by 8 bp out of 264 bp, and by 1 amino acid out of 88. FIG. 3 shows an alignment of these sequences. The sequences of these genomic amplicons confirmed the existence of the IgY CH1 and CH2 pseudo exons observed in the Oxford Nanopore genome assembly.

Figure 5:
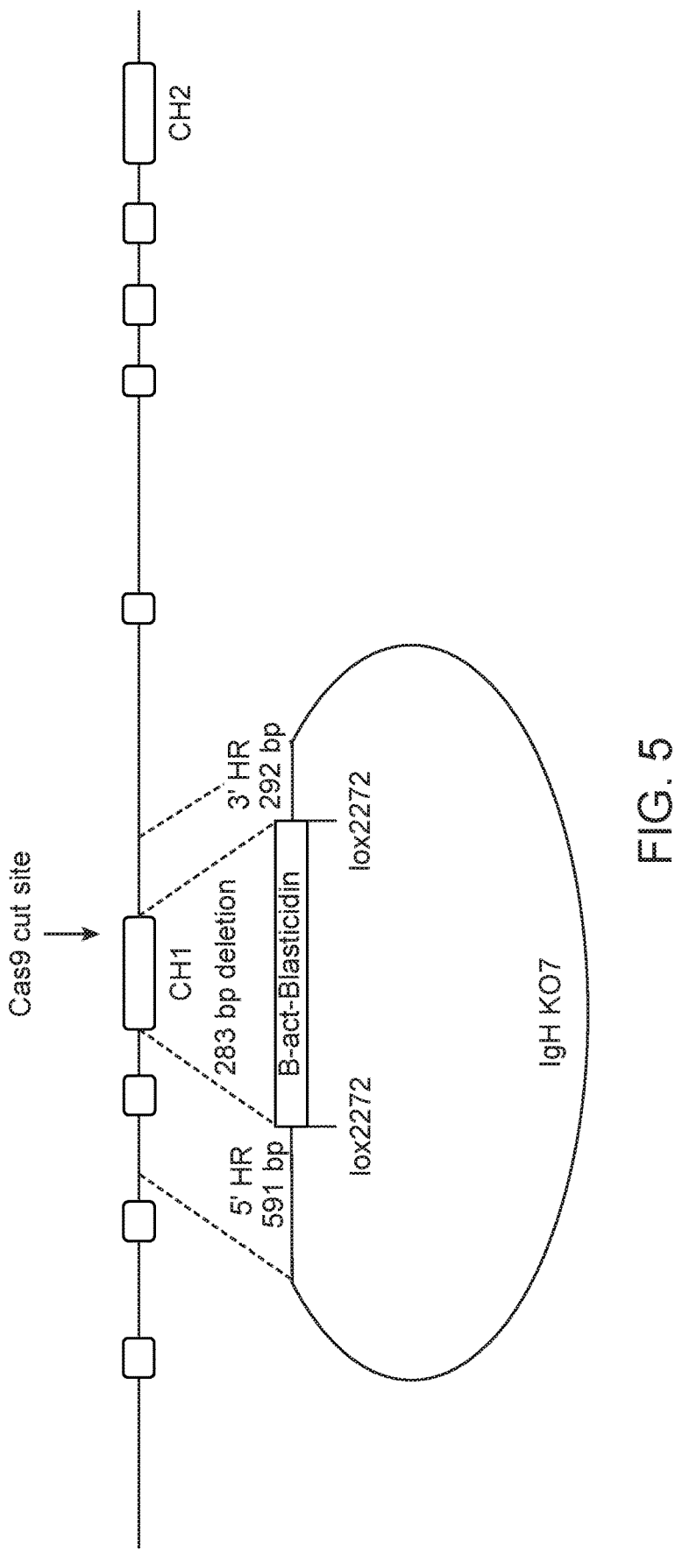
FIG. 5 illustrates the strategy to delete CH1 exon in PGCs. Circular IgH KO7 was co-transfected with a plasmid expressing Cas9 and a guide RNA designed to cut in the CH1 exon. Several different gRNAs were tried, in individual transfections with IgH KO7. The gRNAs were designed to cut in CH1 at a distance of 0-107 bp from the 3' homology region. All of the gRNAs were designed toward the 3' end of the CH1 exon, so as not to cut in any of the pseudo exon sequences. The double strand break or double nicking produced by Cas9 was designed to be repaired by homology-directed repair from IgH KO7. Targeting by IgH KO7 will produce a deletion of 283 bp, including the CH1 exon and 24 bp upstream. The CH1 sequence is replaced by a B-actin-blasticidin ("B-act-Blasticidin") selectable marker, flanked by lox2272 sites for later removal of the selectable marker with Cre.
Figure 6:
FIG. 6 illustrates the targeting vector IgH KO7, used to delete the CH1 exon in PGCs.

Targeting vector IgH KO7 was built with homology regions of 591 bp and 292 bp on either side of a B-actin-blasticidin selectable marker. The b-actin-blasticidin is flanked by lox2272 sites for later removal of the selectable marker cassette by Cre recombination in birds. LoxP sites are situated upstream in 1783-10, surrounding selectable markers used in inserting the human V regions, but they should not recombine with the lox2272 sites. Cre will thus remove the selectable markers in both areas of the modified IgH locus at the same time. The strategy for deleting the CH1 exon in PGCs is shown in FIG. 5 and a map of the K07 vector is shown in FIG. 6.

Figure 4:
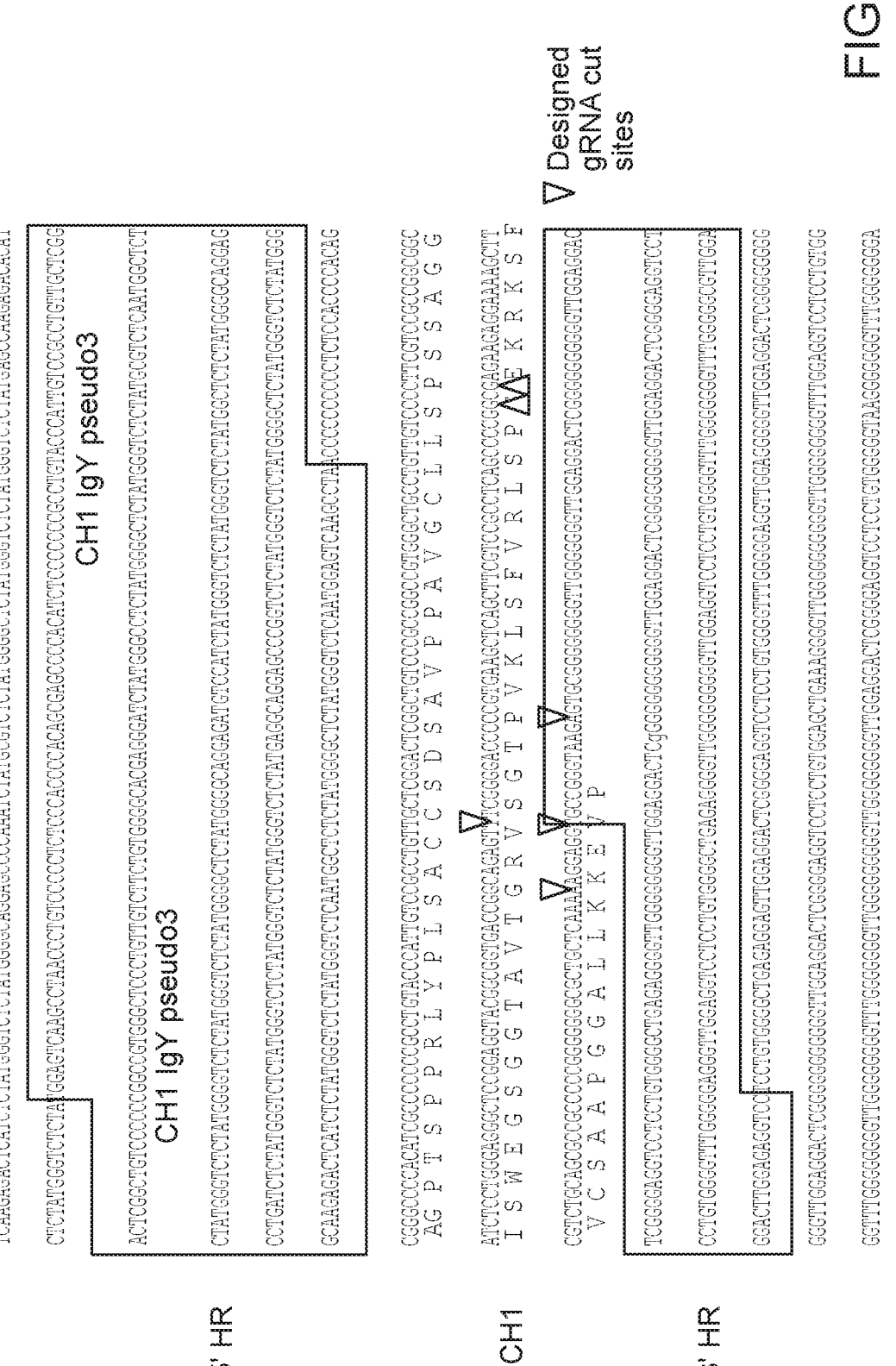
FIG. 4 provides a detailed map of the 5' and 3' homology regions (HRs) relative to the IgY CH1 coding exon (with translation shown). The gRNA cut sites are shown as arrowheads. The orientation of the arrowhead indicates the strand that is cut; pointing down indicates the forward (shown) strand is cut, pointing up indicates the reverse (not shown) strand. SEQ ID NOS 3 and 4.

To increase the efficiency of targeting by IgH KO7, we employed CRISPR/Cas9 to engineer a double strand break in the CH1 exon. The double strand break is repaired by homology-directed repair by the IgH KO7 vector, leading to deletion of the CH1 exon and replacement with the b-actin-blasticdin gene. We utilized either a wild type Cas9 nuclease or a mutant Cas9 that only nicks one strand of the DNA. To direct the cutting of the DNA to the CH1 exon, we designed guide RNAs (gRNAs) using algorithms on the Benchling platform or the Zhang lab/MIT server. A detailed map of the cut sites is shown in FIG. 4. The sequences of the gRNAs designed to direct cutting the IgY CH1 exon are shown in FIG. 7. The gRNAs were designed to the 3' half of the CH1 exon, as this part of the sequence was not found in any of the pseudo exons. We avoided gRNAs that might direct cutting to the pseudo exons so as to avoid additional potential DNA breaks and genomic rearrangements. Six gRNAs were cloned individually into a vector which also contains an expression cassette for the Cas9 nuclease, producing six vectors, each one expressing one of the gRNAs plus Cas9. These vectors supply the gRNA and Cas9 upon transfection into PGCs, directing the cutting to the desired location. In the case of the nicking Cas9 enzyme, two gRNAs were cloned into the same vector so that double nicking of the genomic DNA at two positions close to each other would occur. PGCs containing the CH1 to be deleted were co-transfected with IgH KO7 and the gRNA/Cas9 constructs, and selected for blasticidin resistance at 3-8 μg/ml blasticidin for at least one week. Cultures of transfected cells were selected in bulk, not as clones arising from a single cell, so the cultures could be a mixture of targeted (IgY CH1 deletion) and non-targeted cells (where IgH KO7 integrated at another genomic site, not CH1). For screening, PCR assays were designed in which one of the primers bound a site in the B-actin-blasticidin cassette, and the other primer in the IgY CH1 flanking region not present on the IgH KO7 targeting vector. A unique, short, non-coding sequence from the human genome was included in the IgH KO7 vector to act as a unique primer binding site for the 5' targeting assay, and the BSD blasticidin gene was used as sequence for primer binding sites for the 3' targeting assay. Positive control templates for the PCR assays were prepared, in which the flanking IgY CH1 sequences are placed adjacent to the IgH KO7 selectable marker and homology regions. Negative controls included parental 1783-10 cells, the BRL feeder layer cells, and other chicken samples.

---

What is claimed is:

1. A transgenic chicken whose genome comprises an endogenous immunoglobulin heavy chain (IgH) gene with a deletion of a CH1 coding sequence in a heavy chain constant (CH) IgY gene segment, wherein the chicken is capable of producing IgY heavy chains that lack a functional CH1 domain.

2. The transgenic chicken of claim 1, wherein the endogenous IgH gene further comprises a deletion of a CH1 coding sequence in a CH IgM gene segment, wherein the chicken is capable of producing IgM heavy chains that lack a functional CH1 domain.

3. The transgenic chicken of claim 1, wherein the deletion of the CH1 coding sequence is a deletion of at least 50% of the CH1 coding sequence.

4. The transgenic chicken of claim 1, wherein the genome of the chicken further comprises a deletion of an endogenous immunoglobulin light chain (IgL) gene.

5. The transgenic chicken of claim 1, wherein the chicken is homozygous for the deletion of the CH1 coding sequence.

6. The transgenic chicken of claim 1, wherein the chicken is heterozygous for the deletion of the CH1 coding sequence.

* * * * *